US010029900B2

(12) United States Patent
Abelli et al.

(10) Patent No.: US 10,029,900 B2
(45) Date of Patent: Jul. 24, 2018

(54) TREATMENT APPARATUS, USING A STERILIZING SUBSTANCE, FOR CLOSURES FOR CONTAINERS (71) Applicant: GEA PROCOMAC S.P.A., Sala Baganza (IT)

(72) Inventors: Paolo Abelli, Parma (IT); Fabio Callegari, Salsomaggiore Terme (IT)

(73) Assignee: GEA PROCOMAC S.P.A., Sala Baganza (IT)

( * ) Notice: Subject to any disclaimer, the term of this patent is extended or adjusted under 35 U.S.C. 154(b) by 397 days.

(21) Appl. No.: 14/762,153

(22) PCT Filed: Jan. 30, 2014

(86) PCT No.: PCT/IB2014/058670
§ 371 (c)(1),
(2) Date: Jul. 20, 2015

(87) PCT Pub. No.: WO2014/140948
PCT Pub. Date: Sep. 18, 2014

(65) Prior Publication Data
US 2015/0367009 A1 Dec. 24, 2015

(30) Foreign Application Priority Data

Mar. 11, 2013 (IT) .............................. PR2013A0016

(51) Int. Cl.
*B67B 3/00* (2006.01)
*A61L 2/16* (2006.01)
(Continued)

(52) U.S. Cl.
CPC ................ *B67B 3/003* (2013.01); *A61L 2/16* (2013.01); *A61L 2/186* (2013.01); *A61L 2/208* (2013.01); *A61L 2/22* (2013.01); *A61L 2209/15* (2013.01)

(58) Field of Classification Search
CPC .... B67B 3/003; B65G 59/107; B65G 59/108; B65G 59/06; B65G 59/061; B65G 59/062;
(Continued)

(56) References Cited

U.S. PATENT DOCUMENTS 4,348,816 A * 9/1982 Arippol .................... F26B 15/18
198/416
4,807,780 A * 2/1989 Parsons ................ B65G 59/108
141/173
(Continued)

FOREIGN PATENT DOCUMENTS

CN 1334780 A 2/2002
CN 1688484 A 10/2005
(Continued)

*Primary Examiner* — Stephen F Gerrity
*Assistant Examiner* — Joshua Kotis
(74) *Attorney, Agent, or Firm* — Pearne & Gordon LLP (57) ABSTRACT

A treatment apparatus (1), using a sterilizing substance, for closures (2) for containers, including:

a rotating unit (6);

a plurality of longitudinal rails (7) able to house the closures (2) arranged by force of gravity, the rails (7) being solidly connected to the rotating unit (6) and being arranged such as to follow a circumferential extension of the rotating unit (6);

dispensing apparatus (16) of the sterilizing substance, a variable-height support profile (15) located below the rails (7) and also having a circumferential extension such as to support the lines (8) of closures (2).

12 Claims, 10 Drawing Sheets (51) Int. Cl.
    *A61L 2/20*     (2006.01)
    *A61L 2/22*     (2006.01)
    *A61L 2/18*     (2006.01)

(58) Field of Classification Search
    CPC . B65G 59/063; B65G 59/066; A61L 2209/15; A23L 3/06
    USPC ...... 53/167, 290, 426, 306–312; 422/22, 24, 422/26, 28, 292, 300–302; 193/44–48; 198/416, 533
    See application file for complete search history.

(56) References Cited

U.S. PATENT DOCUMENTS

| | | | |
|---|---|---|---|
| 4,958,649 A | | 9/1990 | Petho |
| 5,244,076 A | * | 9/1993 | Bachmann ............. B65D 88/68 198/443 |
| 5,251,423 A | * | 10/1993 | Turtschan ............... B65B 55/10 53/167 |
| 6,302,259 B1 | * | 10/2001 | Heuft ................... B65G 47/244 198/416 |
| 7,353,643 B2 | | 4/2008 | Cirio |
| 7,360,345 B2 | | 4/2008 | Topf |
| 8,834,808 B2 | | 9/2014 | Drenguis |
| 2005/0169796 A1 | * | 8/2005 | Krakers ................. A61L 2/202 422/28 |
| 2005/0247028 A1 | | 11/2005 | Topf |
| 2007/0157552 A1 | | 7/2007 | Cirio |
| 2009/0077930 A1 | * | 3/2009 | Buchhauser ............ A61L 2/208 53/426 |
| 2009/0129975 A1 | | 5/2009 | Colato et al. |
| 2011/0138740 A1 | * | 6/2011 | Evers ..................... B67B 3/003 53/167 |
| 2011/0142731 A1 | * | 6/2011 | Beckmann ............. A61L 2/208 422/292 |
| 2013/0004368 A1 | * | 1/2013 | Morita .................... A61L 2/22 422/28 |
| 2013/0052089 A1 | | 2/2013 | Drenguis |
| 2013/0193344 A1 | | 8/2013 | Drenguis |

FOREIGN PATENT DOCUMENTS

| | | | | |
|---|---|---|---|---|
| CN | 1986378 A | | 6/2007 | |
| CN | 101237893 A | | 8/2008 | |
| DE | 102010025541 A1 | | 12/2011 | |
| DE | 10 2010 052 207 A1 | | 5/2012 | |
| EP | 1 547 622 A1 | | 6/2005 | |
| EP | 1749747 A1 | | 2/2007 | |
| EP | 1 801 066 A2 | | 6/2007 | |
| EP | 1890730 A2 | | 2/2008 | |
| EP | 2 246 176 A1 | | 11/2010 | |
| EP | 2039439 A1 | | 12/2010 | |
| EP | 2 279 850 A1 | | 2/2011 | |
| GB | 2177923 A | * | 2/1987 | ............. B65B 55/10 |
| WO | 0046142 A1 | | 8/2000 | |
| WO | 2006128884 A2 | | 12/2006 | |
| WO | 2010/023697 A1 | | 3/2010 | |
| WO | 2010/031464 A2 | | 3/2010 | |
| WO | 2012/000573 A1 | | 1/2012 | |

\* cited by examiner

TREATMENT APPARATUS, USING A STERILIZING SUBSTANCE, FOR CLOSURES FOR CONTAINERS

FIELD OF THE INVENTION

The present invention relates to a treatment apparatus, using a sterilizing substance, for closures for containers. In particular, the apparatus of the invention is applicable to the field of bottling using aseptic technology.

DESCRIPTION OF RELATED ART

As is known, in a bottling line with aseptic technology, contamination control in the various work stations (forming, filling, capping, etc.) is of primary importance. It is essential to ensure an adequate filtering of the fluids to be placed inside the controlled environment, proper management of the pressures of the various areas so as to control the path of any unwanted particles, correct monitoring of the environment, proper management and adequate quality of CIP ("Cleaning In Place") and S.I.P. sterilization ("Sterilization In Place") cycles.

The Applicant has recently developed an isolating apparatus able to define a contamination-controlled environment housing the various work stations of a bottling line, such as sterilization of the preform, container forming, filling of the formed containers and closing the filled containers. The apparatus and the method therefore are described in detail in European Patent EP2246176 and in European patent application EP2279850 in the name of the present Applicant.

In an aseptic bottling line, before the filling of the formed containers and the capping thereof, there is also a need to sterilize the closures (caps or capsules) of the containers themselves. In the prior art, the closures can be sterilized either using chemical agents, or with the use of electromagnetic radiation. The invention disclosed in the present application concerns sterilization using chemical agents; therefore a brief description will now follow of the main chemical sterilizing solutions at present known.

Document WO2010031464 describes an apparatus for sterilizing caps internally of rotating transport system. The caps, organized substantially horizontally in lines and spaced from one another, follow a path along an endless conveyor belt associated with a motor and a pulley and, during this path, are subjected to treatment with a sterilizing agent. The proposed apparatus is structurally complex and bulky, since it also carries out the orientating of the caps on the conveyor belt.

Another solution, described in the document EP2039439, provides for the sterilization of capsules by immersion in peracetic acid during the advancement along a spiral path.

The treatment of the capsules shown in the document U.S. Pat. No. 7,360,345 includes the presence of a plurality of rotating discs able to support the capsules internally of a very compact drum. The main disadvantage of this solution is related to the complexity of the transfer of the capsules from one disc to another.

Another solution is represented by the document WO2010023697, in which the capsules are sterilized internally of a linear conduit in which the sterilizing substance is dosed.

Other solutions instead include advancing the capsules by force of gravity and sterilizing them along the advancement path thereof.

For example, document U.S. Pat. No. 4,958,649 describes an apparatus formed by a plurality of involuted channels arranged on a circular base bearing the capsules, which advance by force of gravity during the treatment.

The solution proposed in EP1547622 instead describes a non-rectilinear advancement path of the capsules, which extends in the plane parallel to the main plane identified by the capsules.

Lastly, document WO2012000573, which represents the closest prior art to the present invention, discloses two superposed independent rotors, each bearing a plurality of vertical rails in which the capsules are introduced by force of gravity. In the first rotor (higher) the capsules are preheated, and in the passage from the first to the second rotor they are treated with the sterilizing substance, and in the second rotor (lower) they are subjected to hot gas flows that activate the sterilizing substance.

The main drawback of this solution is the following. The capsules, as mentioned, are arranged in vertical lines in the corresponding rails and, during rotation, remain substantially in position. The sterilizing substance thus reaches the exposed areas of each capsule, i.e. the internal surface and a large part of the external surface. However, there are "grey areas" that are not affected by the sterilizing substance: these are areas of relative contact between the capsules. These grey areas are unlikely to be sterilized or will be insufficiently sterilized.

OBJECT OF THE INVENTION

In this context, the technical objective underpinning the present invention is to provide a treatment apparatus, using a sterilizing substance, for closures for containers, which obviates the drawbacks of the above-mentioned prior art.

In particular, the aim of the present invention is to disclose a treatment apparatus, using a sterilizing substance, for closures for containers which enables obtaining a more uniform sterilization of each closure.

A further aim of the present invention is to make available a treatment apparatus of closures for containers by means of a sterilizing substance which apparatus is compact, structurally simple and, at the same time, more effective than the known solutions.

The set technical objective and the aims specified are substantially attained by a treatment apparatus, using a sterilizing substance, for closures for containers, comprising the technical characteristics set out in one or more of the appended claims.

BRIEF DESCRIPTION OF THE DRAWINGS

Further characteristics and advantages of the present invention will more fully emerge from the description given by way of non-limiting example of a preferred but not exclusive embodiment of a treatment apparatus, using a sterilizing substance, for closures for containers, with a sterilizing substance, as illustrated in the appended drawings, in which.

DETAILED DESCRIPTION OF PREFERRED EMBODIMENTS OF THE INVENTION

With reference to the figures, reference numeral 1 denotes a treatment apparatus, using a sterilizing substance, for closures 2 for containers. For example, the sterilizing substance is hydrogen peroxide. In particular, the sterilizing substance is gaseous. Alternatively, the sterilizing substance is liquid.

In this context, the term closure 2 relates to a concave closure such as a cap or a capsule. The closure 2 is preferably made of a polymer material.

Figure 7A:
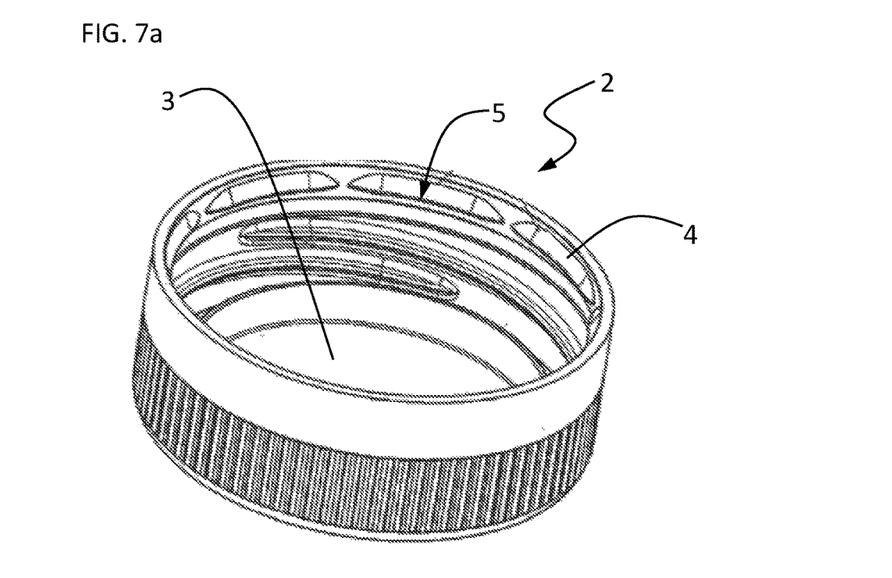
FIGS. 7a and 7b illustrate two different closures, respectively a flat cap and a sports cap, in perspective views.

For example, the closure 2 is represented by a flat cap, as illustrated in FIG. 7a. Another example of a closure 2 is represented by the sports cap shown in FIG. 7b.

Figure 7B:
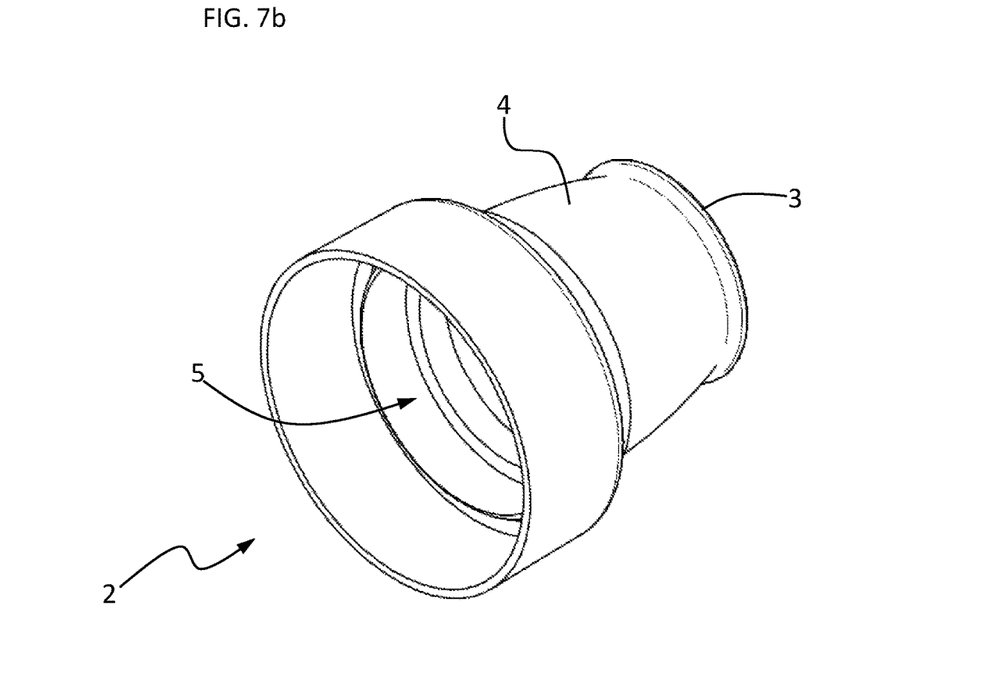

In both cases, the closure 2 has a base 3 and a lateral wall 4 extending from the base 3 and defining therewith a cavity 5. The cavity 5 is open: in fact, on the side opposite the base 3 the closure 2 has an opening that can accommodate the mouth of a container so that the lateral wall 4 can engage therewith and the base 3 can close it.

In this context, the term "internal surfaces" of the closure 2 identifies the internal surface of the lateral wall 4 and the internal surface of the base 3. The term "external surfaces" of the closure 2 refers to the external surface of the lateral wall 4 and the external surface of the base 3.

In FIG. 7a the cavity 5 delimited by the closure 2 exhibits a substantially cylindrical shape, so that the lateral wall 4 corresponds substantially to the lateral wall of a cylinder and the base 3 is a circular disc. Alternatively, the cavity 5 delimited by the closure 2 has a slightly conical shape.

The sports cap 2 of FIG. 7b exhibits a more complex shape, though the base 3, the lateral wall 4 and the cavity 5 can also be identified therein.

The treatment apparatus 1 comprises a rotating unit 6 and a plurality of longitudinal rails 7 able to house the closures 2 arranged by force of gravity in a same number of lines 8. The rails 7 are substantially parallel to one another and are solidly connected to the rotating unit 6 in such a way as to follow the circumferential extension thereof.

In the embodiment described and illustrated herein, the rails 7 are parallel to the rotation axis A of the rotating unit 6.

In all the accompanying figures the treatment apparatus 1 is positioned on a support plane (ground or floor) in such a way that the rotation axis A of the rotating unit 6 is perpendicular to the support plane. Therefore, the rails 7 are also perpendicular to the support plane (as they are parallel to the rotation axis A).

There is also the possibility (not illustrated) of arranging the treatment apparatus 1 with the rotation axis A inclined with respect to the support plane. In this case, the rails 7 are also inclined with respect to the support plane (as they are parallel to the rotation axis A).

In an alternative embodiment (not illustrated), the rails 7 are inclined by a predetermined angle relative to the rotation axis A of the rotating unit 6.

The treatment apparatus 1 comprises a protection casing 9 able to define and isolate a controlled-contamination internal environment 10. For example, the protection casing 9 defines an internal environment 10 substantially in the shape of an octagonal prism or having a cylindrical shape.

In particular, the protection casing 9 comprises heating means for the walls of the casing 9 itself, which are in contact with the controlled-contamination internal environment 10. The heating means include means for controlling the temperature of the walls in order to avoid condensation. The heating means are made in known ways. The protection casing 9 is provided with at least an access window 11 enabling interventions for regulating and/or maintenance of the controlled-contamination internal environment 10. In the embodiment described and illustrated herein, there are three access windows 11 closable by means of corresponding airtight hatch doors 12.

Figure 4:
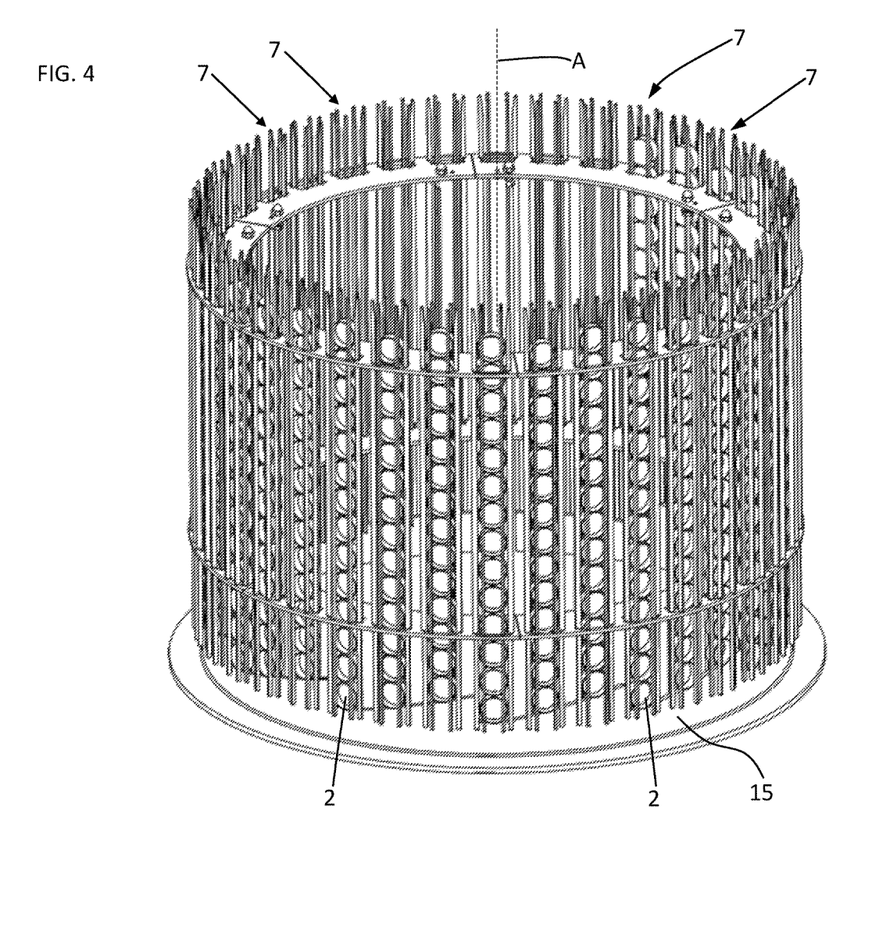
FIG. 4 illustrates a portion of the treatment apparatus of FIG. 1 (rails, support profile), in a perspective view.

Each closure 2 housed in the rails 7 exhibits the cavity 5 (and therefore the opening) facing outwards (see for example FIG. 4). In other words, the cavity 5 (and therefore the opening) is facing towards the protection casing 9.

The treatment apparatus 1 is preferably provided with conveying means 13 of the closures 2 towards the internal controlled-contamination environment 10. For example, the conveying means 13 comprise at least a channel 13a on which the closures 2 advance by force of gravity. The channel 13a is preferably substantially vertical. Alternatively, the channel 13a is inclined.

The protection casing 9 preferably exhibits an upper base 9a in which an opening 14 is afforded for access, into which the conveyor channel 13a opens.

The treatment apparatus 1 comprises a support profile 15 located below the rails 7 and also having a circumferential extension for supporting the lines 8 of closures 2.

In the embodiment described and illustrated herein, the support profile 15 is fixed with respect to the rotating unit 6. In an alternative embodiment (not shown), the support profile 15 is mobile with respect to the rotating unit 6.

The treatment apparatus 1 comprises dispensing means 16 of the sterilizing substance. In the embodiment described and illustrated herein, the dispensing means 16 are fixed in relation to the rotating unit 6. Alternatively, the dispensing means 16 are mobile.

Figure 1:
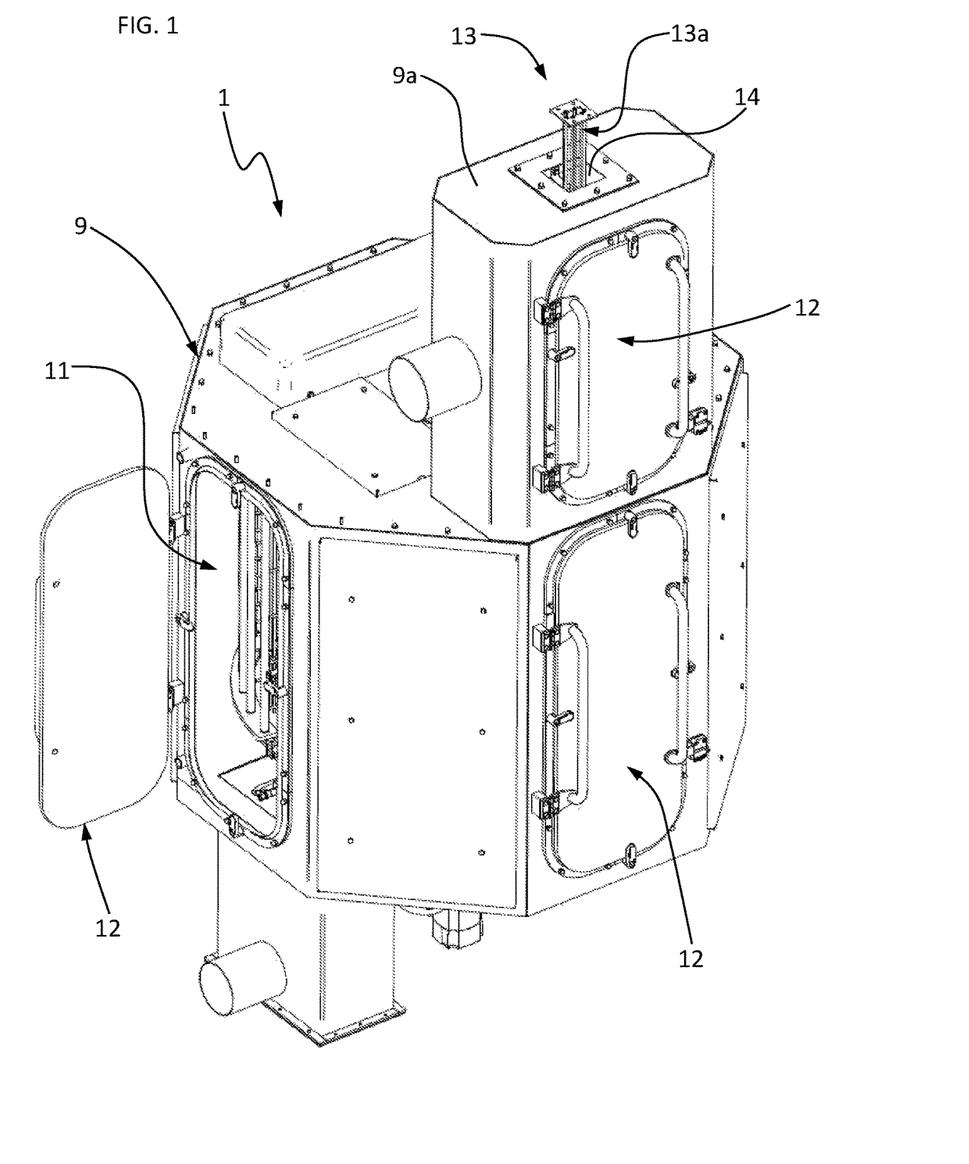
FIG. 1 illustrates a treatment apparatus, using a sterilizing substance, for closures for containers, in a perspective view from above.
Figure 2:
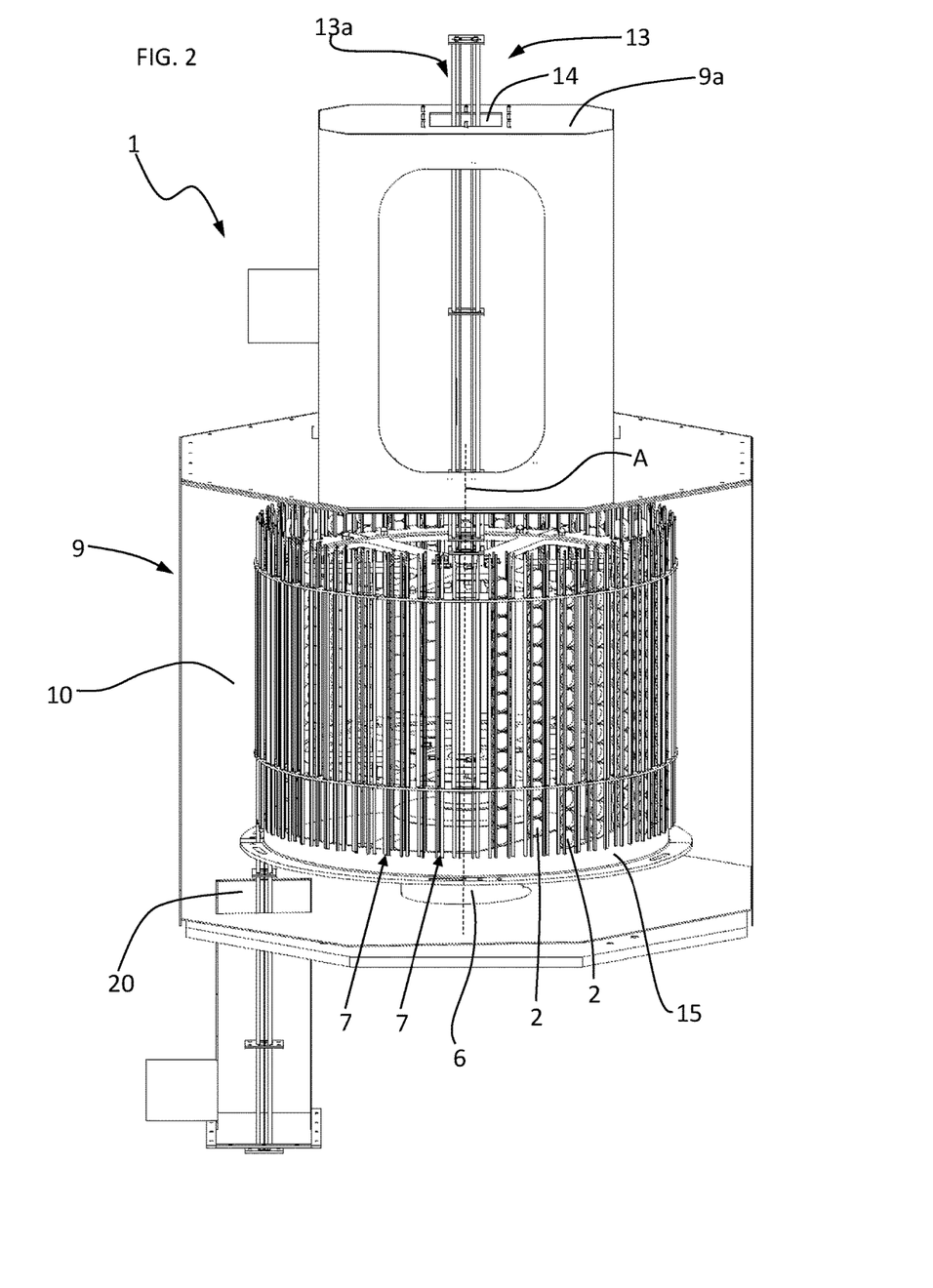
FIG. 2 illustrates the treatment apparatus of FIG. 1 (in which the protection casing has been partially removed), in a frontal perspective view.
Figure 3:
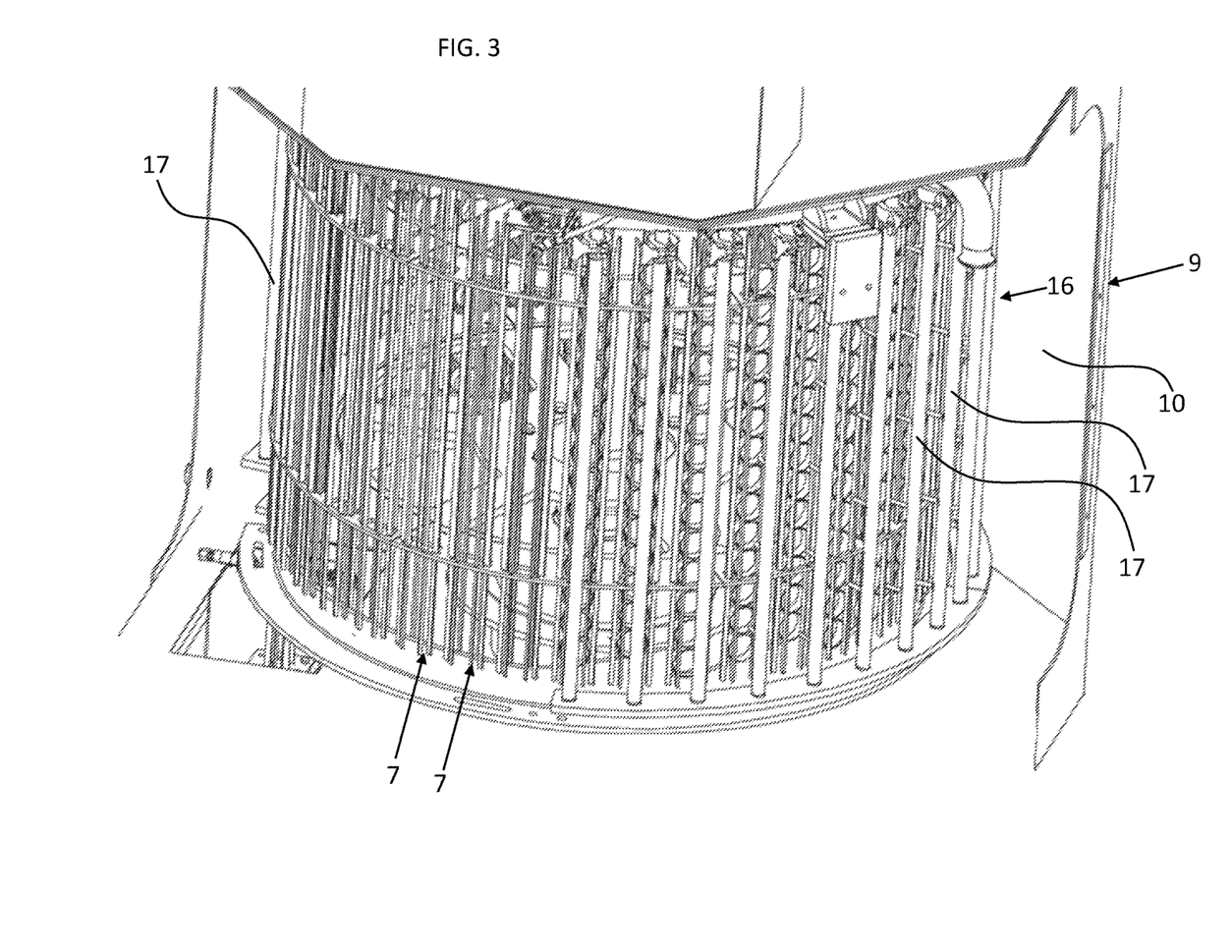
FIG. 3 illustrates a portion of the treatment apparatus of FIG. 1 (rotating unit, rails, dispensing means), in a perspective view.

In particular, the dispensing means 16 comprise a plurality of nozzles arranged in such a way as to deliver the sterilizing substance towards the cavities 5 of the closures 2. In particular, the nozzles are positioned between the rails 7 and the protection casing 9 and therefore they also follow a circumferential extension. In other words, the dispensing means 16 define a concentric circumferential extension with a larger diameter than the circumferential extension of the housing rails 7 of the closures 2 (see FIG. 3). In the embodiment described and illustrated herein the dispensing means 16 consist of tubular bodies 17 arranged substantially vertically, i.e. parallel to the rails 7. Each of these tubular bodies 17 exhibits a plurality of nozzles.

Originally, the support profile 15 has a variable height in such a way that, with the rotating unit 6 in rotation, the lines 8 of closures 2 follow a circumferential path with level differences that can cause the relative displacements between the closures 2.

Figure 6A:
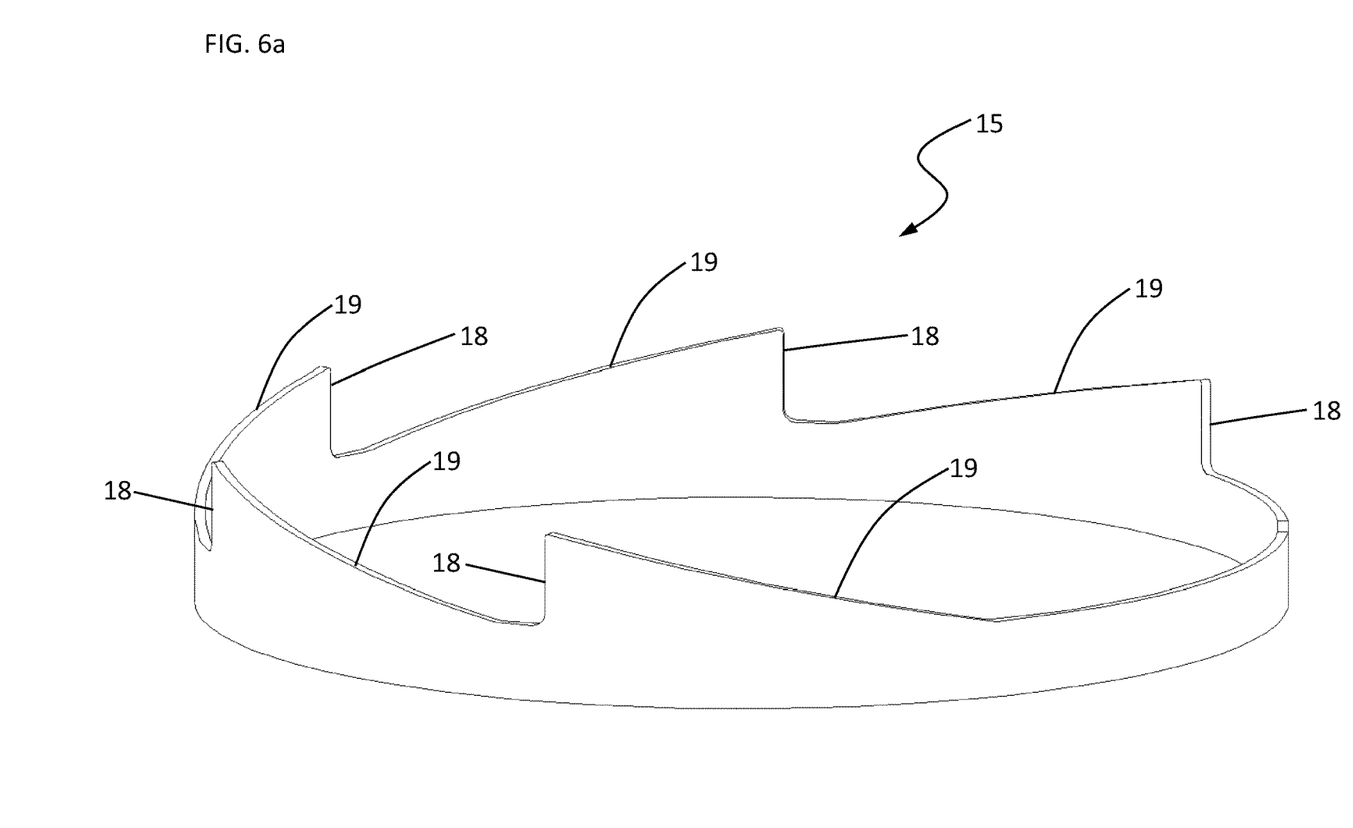
FIGS. 6a, 6b and 6c illustrate three embodiments of the support profile of the treatment apparatus of FIG. 1, in a perspective view.
Figure 6B:
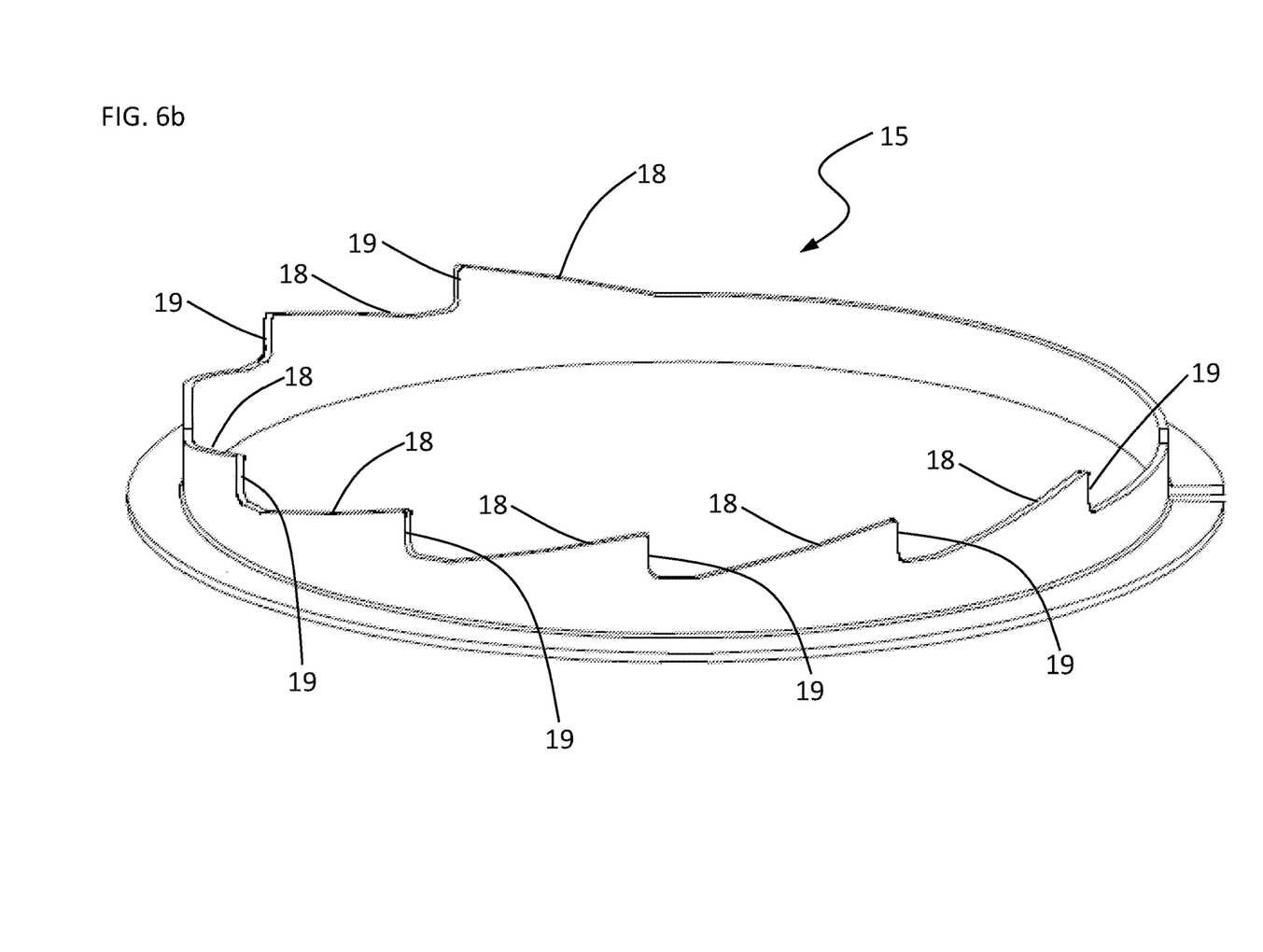
Figure 6C:
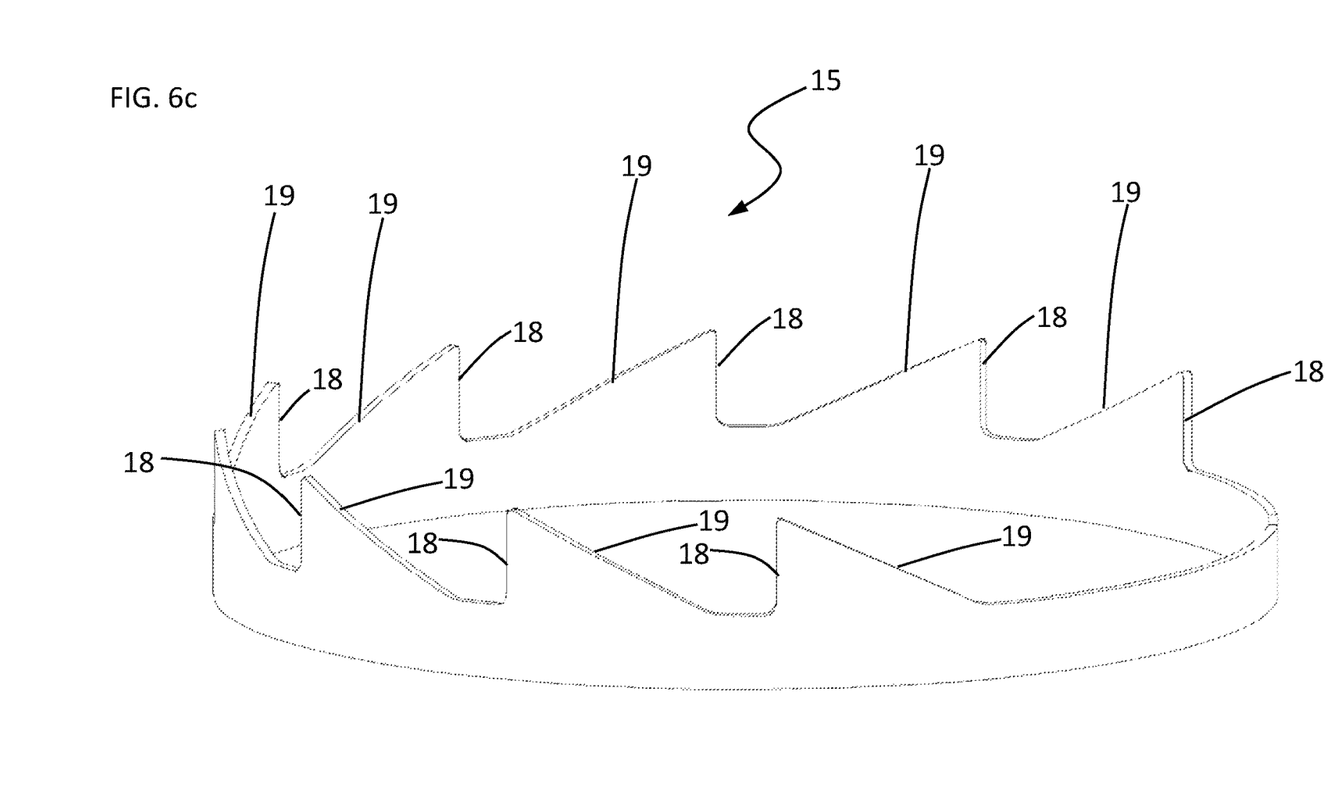

The level differences circumferential path comprises at least a rising section 18 and at least a descending section 19. In the embodiments described and illustrated herein, the circumferential path with level differences comprises a plurality of rising sections 18 and a plurality of descending sections 19. For example, the rising sections 18 and descending sections 19 are ramps having a predetermined inclination, or are steps.

The functioning of the treatment apparatus, using a sterilizing substance, for closures for containers according to the present invention, will be described in the following. Consider the rotating unit 6 initially in a stationary state.

The closures 2 advance by force of gravity in the conveyor channel 13a and, when passing through the access opening 14, are arranged in the rail 7 positioned immediately below the access opening 14, thereby forming a first line 8. As mentioned above, each closure 2 is arranged with the cavity 5 facing the protection casing 9.

Figure 5A:
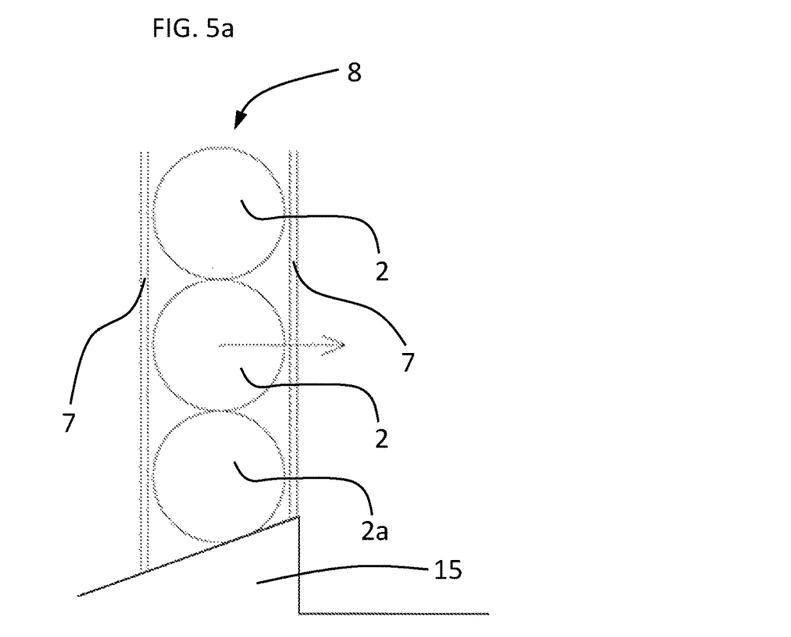
FIGS. 5a and 5b schematically illustrate the relative position of a line of closures with respect to the support profile at two different instants of rotation of the rotating unit.

The closure 2a of the line 8 which is located at a lower level (which for the sake of clarity we will call the head closure 2) rests on the support profile 15, as shown in FIG. 5a.

During the rotation of the rotating unit 6, the rails 7 rotate solidly with the rotating unit 6 and the closures 2 in arrival from the conveyor channel 13a are unloaded one after another into the rail 7 positioned below the access opening 14.

Figure 5B:
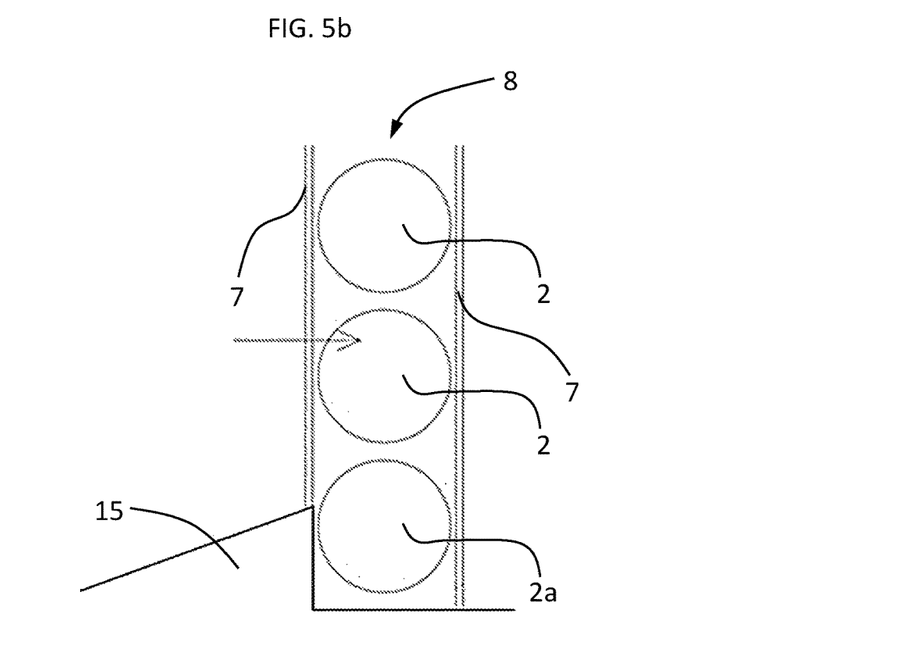

The rotation of the rails 7 causes the head closure 2a of each line 8 to follow the circumferential path with level differences along the rising sections 18 and descending sections 19. For example, FIGS. 5a and 5b illustrate a head closure 2a descending from a step of the support profile 15. This step causes the separation of the closures of the line 8 during the descent, thus removing the areas of contact between a closure 2 and another. Moreover, as it descends from the step, the head closure 2a partially rotates on itself, causing in turn the rotation of the closure 2 positioned immediately above.

During the rotation, the dispensing means 16 spray the sterilizing substance towards the cavities 5 of the closures 2, so that the internal surfaces of the closures 2 are sterilized. During normal operation, all the internal environment 10 is saturated with a sterilizing substance, so that the external surfaces of the closures 2 are sterilized.

In addition, the separations that are created between the closures 2 during the drop from step and the partial rotations of the closures 2 themselves modify the momentary contact zones between the closures 2.

At the end of a partial or complete revolution of the rotating unit 6, the closures 2 are sent to the outside through an outlet opening 20 formed in the protection casing 9.

Figure 8:
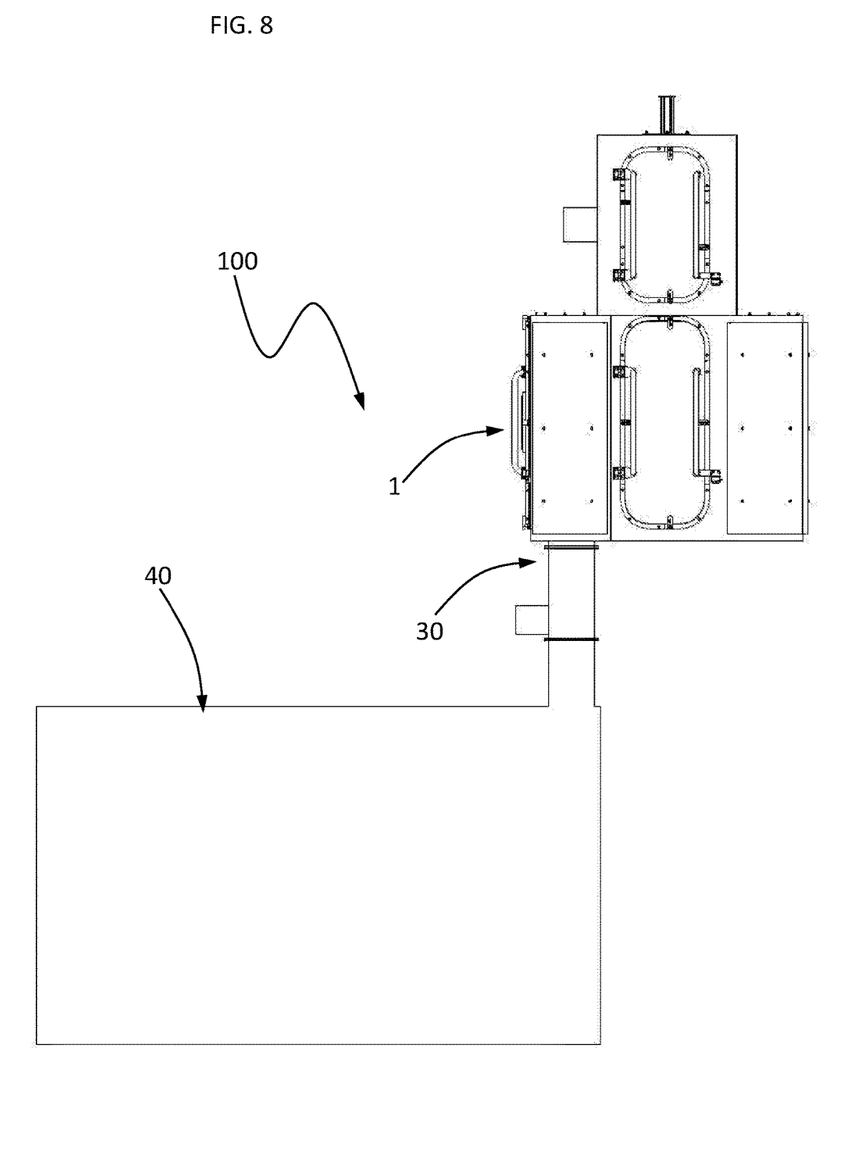
FIG. 8 illustrates a schematic view of a bottling line comprising the treatment apparatus of FIG. 1.

The treatment apparatus 1 is part of a bottling line 100, as shown in FIG. 8.

A filler apparatus 30 of the containers is located downstream of the treatment apparatus 1, which filler apparatus is also isolated and connectable to the treatment apparatus 1 via an interfacing device 40. In the controlled-contamination internal environment 10 of the treatment apparatus 1 the pressure is around 10 Pa. The pressure inside the filler apparatus 30 is around 30 Pa. The interfacing device 40 exhibits a communication section with the treatment apparatus 1 and a communication section with the filler apparatus 30 dimensioned in such a way as to prevent particles (e.g. of the product) and fluids (e.g. washing fluids) coming from the filler apparatus 30 from reaching the treatment apparatus 1.

The characteristics of the treatment apparatus, using a sterilizing substance, for closures for containers, according to the present invention, are clear from the foregoing description, as are the resulting advantages.

In particular, thanks to the presence of a variable-height support profile, the closures are subjected to relative displacements during rotation of the rotating unit. These relative displacements ensure that substantially all the areas are gradually exposed to the treatment of the sterilizing substance. In other words, there are no longer "grey areas" inaccessible to the sterilizing substance, and therefore each closure is sterilized in a more uniform way than in the prior art.

Further, the treatment apparatus disclosed herein is structurally simple and compact as the displacements of the closures are caused by the level differences profiling of the support profile. The dimensions of the apparatus are therefore identical to those of the solutions of closest prior art, but the effectiveness of the sterilization is increased.

The invention claimed is:

1. A treatment apparatus (1), using a sterilizing substance, for closures (2) for containers, comprising:
   a rotating unit (6);
   a plurality of longitudinal rails (7) able to house said closures (2) arranged by force of gravity in a plurality of lines (8) corresponding to the plurality of longitudinal rails (7), said rails (7) being substantially parallel to one another and being solidly connected to said rotating unit (6) such as to follow a circumferential portion of the rotating unit (6);
   a support profile (15) located below the rails (7) and having a portion extending in a circumferential direction such as to support the lines (8) of closures (2);
   dispensing means (16) of said sterilizing substance;
   wherein said support profile (15) includes a circumferential path comprising ramped or stepped surfaces such that, with the rotating unit (6) in rotation, the lines (8) of closures (2) follow the circumferential path to cause relative displacements between the closures (2).

2. The treatment apparatus (1) according to claim 1, wherein said rails (7) are parallel to a rotation axis (A) of said rotating unit (6).

3. The treatment apparatus (1) according to claim 2, wherein said rotation axis (A) of the rotating unit (6) is perpendicular to a support plane of the treatment apparatus (1).

4. The treatment apparatus (1) according to claim 2, wherein said rotation axis (A) of the rotating unit (6) is inclined with respect to a support plane of the treatment apparatus (1).

5. The treatment apparatus (1) according to claim 1, wherein said rails (7) are inclined by a predetermined angle with respect to a rotation axis (A) of said rotating unit (6).

6. The treatment apparatus (1) according to claim 1, wherein said support profile (15) is fixed with respect to said rotating unit (6).

7. The treatment apparatus (1) according to claim 1, wherein said dispensing means (16) comprise a plurality of nozzles arranged externally, with respect to a rotation axis (A) of said rotating unit (6), of said rails (7).

8. The treatment apparatus (1) according to claim 1, further comprising a protection casing (9) able to define and isolate an internal controlled-contamination environment (10).

9. The treatment apparatus (1) according to claim 8, further comprising conveying means (13) of the closures (2) towards said controlled-contamination environment (10).

10. The treatment apparatus (1) according to claim 9, wherein said conveying means (13) comprise at least a channel (13a) on which the closures (2) advance by force of gravity, said protection casing (9) having an access opening (14) into which said channel (13*a*) opens.

11. The treatment apparatus (1) according to claim 8, wherein said protection casing (9) comprises walls, said walls being in contact with said internal controlled-contamination environment (10).

12. A bottling line (100) of containers, comprising:
a treatment apparatus (1) according to claim 1;
a filler apparatus (30) of the containers;
an interfacing device (40) between the treatment apparatus (1) and the filler apparatus (30), said interfacing device (40) having a communicating section with the treatment apparatus (1) and a communicating section with the filler apparatus (30) dimensioned such as to prevent particles and fluids coming from the filler apparatus (30) from reaching the treatment apparatus (1).

* * * * *